United States Patent [19]

Pytel et al.

[11] Patent Number: 5,240,007
[45] Date of Patent: Aug. 31, 1993

[54] APPARATUS AND METHOD FOR MOVING A TISSUE STRESS SENSOR FOR APPLANATING AN ARTERY

[75] Inventors: Kenneth J. Pytel, San Diego; Stephen A. Martin, Carlsbad; Robert D. Butterfield, Poway; William R. Ewing, San Diego, all of Calif.

[73] Assignee: IVAC Corporation, San Diego, Calif.

[21] Appl. No.: 700,009

[22] Filed: May 14, 1991

[51] Int. Cl.⁵ ............................................. A61L 5/021
[52] U.S. Cl. ..................................... 128/672; 128/690
[58] Field of Search ............... 128/672, 677, 680, 681, 128/682, 683, 686, 687, 689, 690, 661.08, 666, 667

[56] References Cited

U.S. PATENT DOCUMENTS

| | | | |
|---|---|---|---|
| 2,660,164 | 11/1953 | Hasbrouck, Jr. | 128/680 |
| 3,527,204 | 9/1970 | Lem et al. | 128/683 |
| 3,572,320 | 3/1971 | Gerold et al. | 128/682 |
| 3,935,984 | 2/1976 | Lichowsky et al. | 128/686 |
| 4,202,347 | 5/1980 | Sacks | 128/677 |
| 4,211,289 | 7/1980 | Klein | 128/686 |
| 4,441,504 | 4/1984 | Peterson et al. | 128/677 |
| 4,830,017 | 5/1989 | Perry et al. | 128/677 |
| 4,971,062 | 11/1990 | Hasebe et al. | 128/687 |
| 4,996,156 | 10/1990 | Perry et al. | 128/687 |
| 5,035,243 | 7/1991 | Muz | 128/687 |

FOREIGN PATENT DOCUMENTS 3030566 3/1982 Fed. Rep. of Germany ...... 128/672

*Primary Examiner*—William E. Kamm
*Attorney, Agent, or Firm*—Dykema Gossett

[57] ABSTRACT

An artery applanation actuator for use in a system for noninvasively determining the intra-arterial blood pressure of a user incorporates a fluid actuator to effect movement of a sensor. The movement of the sensor is effective for applanating an artery of interest and measuring the stress of the tissue overlaying the artery of interest. Alternative embodiments of the artery applanation actuator are presented wherein an electric motor is used to activate a rotating arm which has a sensor located thereon. The rotation of the arm causes the sensor to contact and press against the tissue overlaying the artery of interest. The artery applanation actuator is presented having a protective sheath surrounding the sensor to protect the sensor against inadvertent contact.

21 Claims, 5 Drawing Sheets

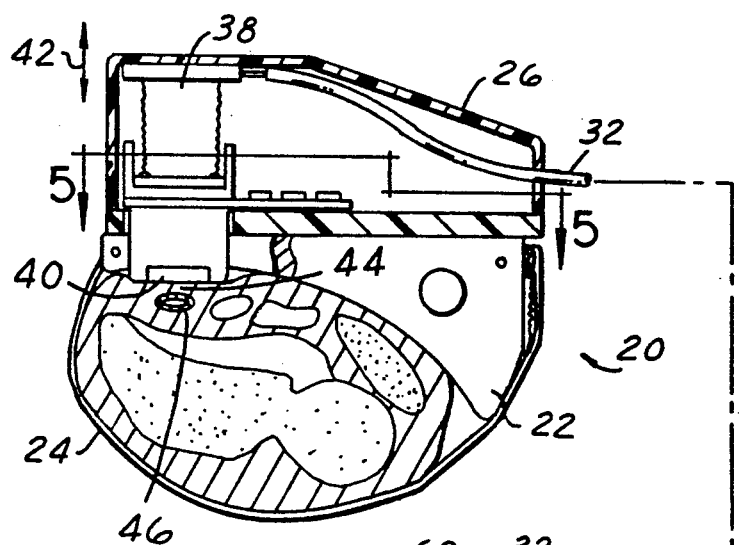
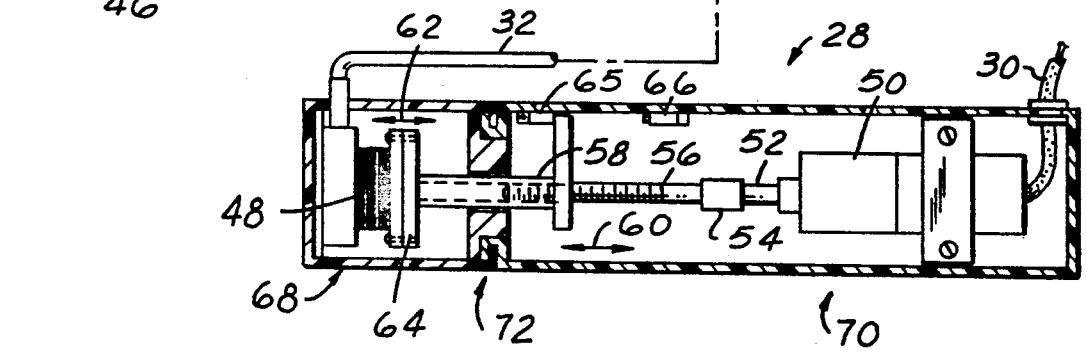
FIG.4
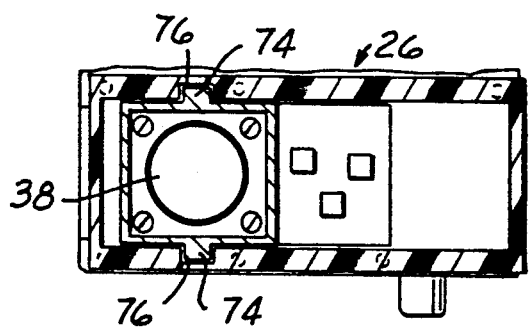
FIG.5
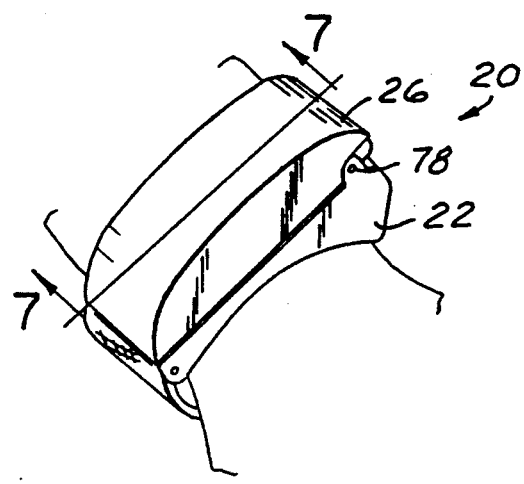
FIG.6

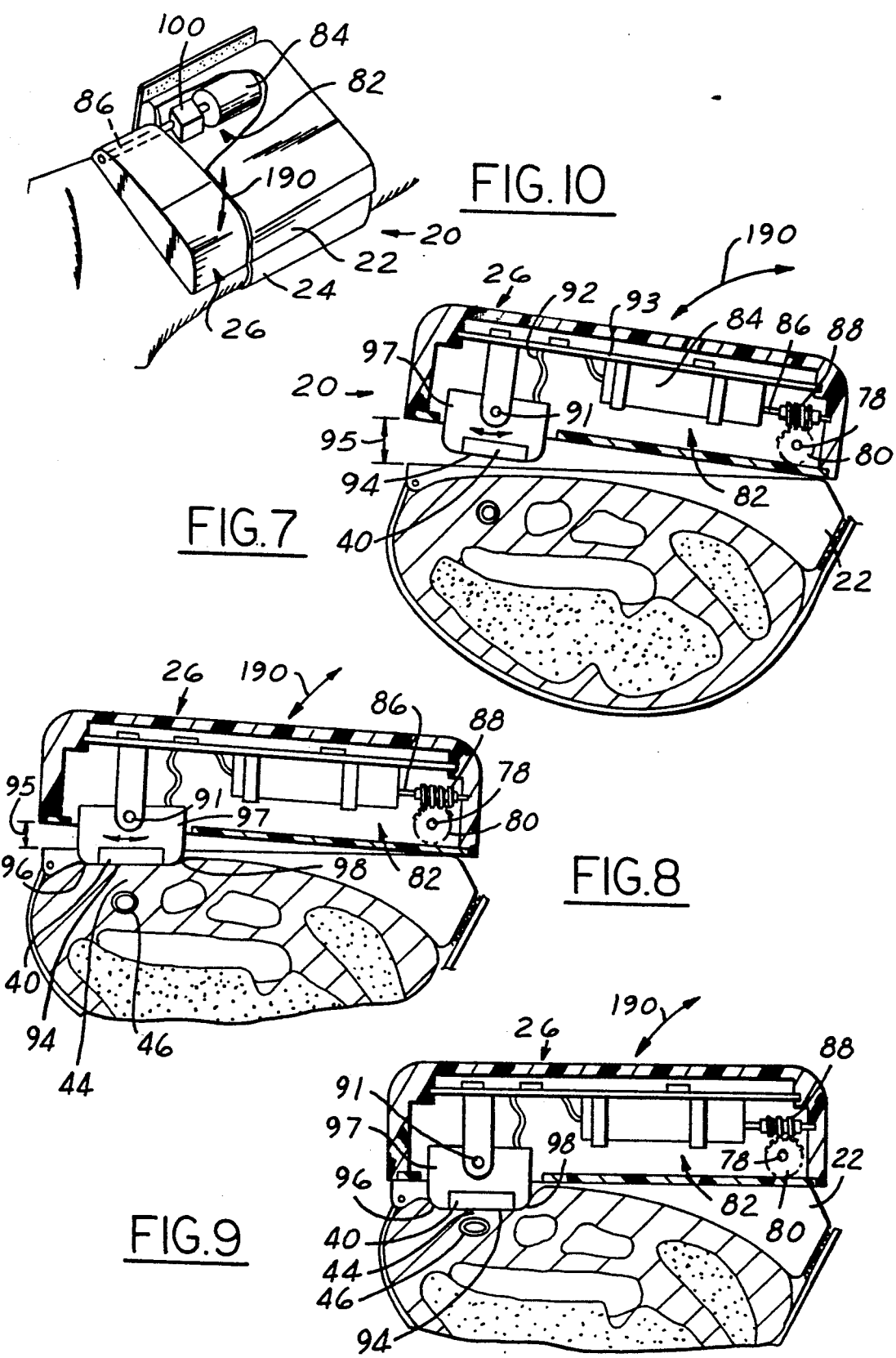

APPARATUS AND METHOD FOR MOVING A TISSUE STRESS SENSOR FOR APPLANATING AN ARTERY

TECHNICAL FIELD

The present invention generally relates to pressure measurement systems, and more particularly relates to an artery applanation apparatus for use in a system for noninvasively determining the intra-arterial blood pressure of a wearer.

BACKGROUND OF THE INVENTION

Systems for measuring the intra-arterial blood pressure of a patient can be subdivided into two main groups—those which invade the arterial wall to access blood pressure and those which use noninvasive techniques. Initially, the most accurate blood pressure measurements were achievable only by use of invasive methods. One such common method involved use of a fluid filled catheter inserted into the patient's artery. While invasive methods provide for accurate blood pressure measurements, the risks of infection and other complications, in many cases, outweigh the advantages of using invasive methods.

Because of the above-mentioned risks associated with invasive methods, a noninvasive method, know as the Korotkoff method is widely used. The Korotkoff method is known as an auscultatory method because it uses, in part, the characteristic sound made as the blood flows through the artery to aid in measuring blood pressure. Although the Korotkoff method is noninvasive, it only provides a measurement of the highest pressure point (systolic) and the lowest pressure point (diastolic) along the pressure wave. While, for many purposes, systolic and diastolic pressure are sufficient, there are many applications in which it is desirable to use the entire characteristic curve of the blood pressure wave. In these applications, the Korotkoff method simply is incapable of providing satisfactory information. In addition to this limitation of the Korotkoff method, it necessitates the temporary occlusion of the artery in which blood pressure is being monitored. While arterial occlusion is not prohibitive in many applications, there are occasions where the patient's blood pressure must be monitored continuously (such as when undergoing surgery) and accordingly, the prohibiting of blood flow, even on a temporary basis, is undesirable.

Because of the above-mentioned risks associated with invasive blood pressure measurement, and the shortcomings of the Korotkoff method, extensive investigation has been conducted in the area of continuous, noninvasive blood pressure monitoring and recording. Some of these noninvasive techniques make use of tonometric principles which take advantage of the fact that as blood flows through the arterial vessel, forces are transmitted through the artery wall, through the surrounding arterial tissue and, consequently, are externally available for monitoring. Because the tonometric method of measuring blood pressure is noninvasive, it is used without the risks associated with invasive techniques. Furthermore, in addition to being more accurate than the Korotkoff method discussed above, it has the capability of reproducing the entire blood pressure wave form, as opposed to the limited systolic and diastolic pressure points provided by the Korotkoff method.

A technique for determining intra-arterial blood pressure involves the method of pressing a sensor against the tissue which overlays an artery of interest thereby flattening, or applanating, the underlying artery. This pressing is applied increasingly harder until a predetermined state of artery applanation is obtained. In this state, certain assumptions can be made regarding the relationship between the forces transmitted to the sensor through the tissue overlaying the artery and the intra-arterial blood pressure. In using this technique to determine intra-arterial blood pressure, it is necessary to provide an apparatus which can applanate the artery with a precise degree of control. Additionally, the artery applanation device should be easy to use and should not unduly restrict the movement of the wearer.

Thus, it is an object of this invention to provide an artery applanation actuator which provides the necessary degree of control to properly effect artery applanation.

It is also an object of this invention to provide an artery applanation actuator which is low profile, lightweight, and comfortable to wear.

SUMMARY OF THE INVENTION

In light of the foregoing objects, the present invention provides an artery applanation actuator for use in a system for noninvasively determining the intra-arterial blood pressure of a wearer. The artery applanation actuator is used for placing a tissue contact stress transducer in operative engagement with the tissue overlying an artery of interest. The artery applanation actuator comprises a base portion which is adapted to be mounted to the wrist of a wearer, and means coupled between the base portion and the tissue stress sensor and responsive to a source of pressurized fluid, for displacing the tissue stress sensor in operative engagement with the tissue overlying the artery of interest, thereby applanating the artery of interest in response to displacing the fluid. Preferably, means for displacing includes a slave bellows and the source of pressurized fluid preferably includes a master bellows. The master bellows communicates with the slave bellows via a fluid medium and the master bellows is responsive to a displacement to communicate the fluid to said slave bellows thereby making the slave bellows responsive to the displacement. The displacement of the fluid is preferably accomplished by way of an electric motor attached to the master bellows. The system preferably includes disconnect means disposed between the electric motor and the master bellows whereby the master bellows is separable from the electric motor while still remaining in fluid communication with the slave bellows. In a preferred embodiment, the displacement source further includes a rotary electric motor and a drive screw, the rotary electric motor being attached to the drive screw and the drive screw being in operative engagement with the master bellows. The electric motor is adapted to turn the drive screw thereby exerting a linear displacement to the master bellows. The master and slave bellows are preferably filled with a hydraulic fluid. Preferably, the displacement source includes a limit switch means for detecting when the drive screw has reached a predetermined limit of travel.

Yet in another aspect, the artery applanation actuator of the present invention includes a base portion adapted to be mounted to the wrist of a wearer, and a sensor head portion for housing the tissue contact stress sensor. A rotary electric means is attached between the base portion and the sensor head portion and made responsive to an electric signal for moving the tissue contact stress sensor into operative engagement with the tissue overlying the artery of interest, thereby causing the tissue stress sensor to applanate the artery of interest. In a preferred embodiment, the electric motor means includes an electric motor having a rotary output shaft. The electric motor is attached to the sensor head portion and the rotary output shaft extends from the sensor head portion and is attached to the base portion. The rotary output shaft preferably includes a gear reduction means.

In a third aspect of the present invention, the electric motor is attached to the base portion and the rotary output shaft extends out from the base portion and is attached to the sensor head portion. The artery applanation actuator preferably includes a protective sheath disposed about the tissue contact stress sensor and pivotally connected about the electric motor shaft. In a preferred embodiment, the sheath includes a spring extending therefrom and attached to the sensor head portion. The sensor head portion preferably includes an arm connected to the rotary output shaft of the electric motor and a transducer assembly pivotally connected to the arm. In this embodiment, the sheath spring extends from the sheath and is attached to the transducer assembly.

Other advantages and meritorious features of the present invention will become more fully understood from the following description of the preferred embodiments, the appended claims and the drawings, a brief description of which follows.

BRIEF DESCRIPTION OF THE DRAWINGS

FIG. 4 is a diagrammatic view of the first embodiment of the artery applanation actuator of the present invention shown applanating an artery.

FIG. 5 is a partial cross-sectional view of the wrist mount portion of the first embodiment of the artery applanation actuator of the present invention taken substantially along lines 5—5 of FIG. 4.

FIG. 6 is a second embodiment of the artery applanation actuator of the present invention shown on a wrist of a wearer.

FIG. 7 is a cross-sectional view of the second embodiment of the artery applanation actuator of the present invention taken substantially along lines 7—7 of FIG. 6.

FIG. 8 is a cross-sectional view of the second embodiment of the artery applanation actuator of the present invention shown with the tissue stress sensor in an intermediate displacement state.

FIG. 9 is a cross-sectional view of the second embodiment of the artery applanation actuator of the present invention shown with the tissue stress sensor head in a maximum displacement state.

FIG. 10 is a perspective view of a third embodiment of the artery applanation actuator of the present invention shown on the wrist of a user.

DETAILED DESCRIPTION OF THE PREFERRED EMBODIMENTS

Figure 1:
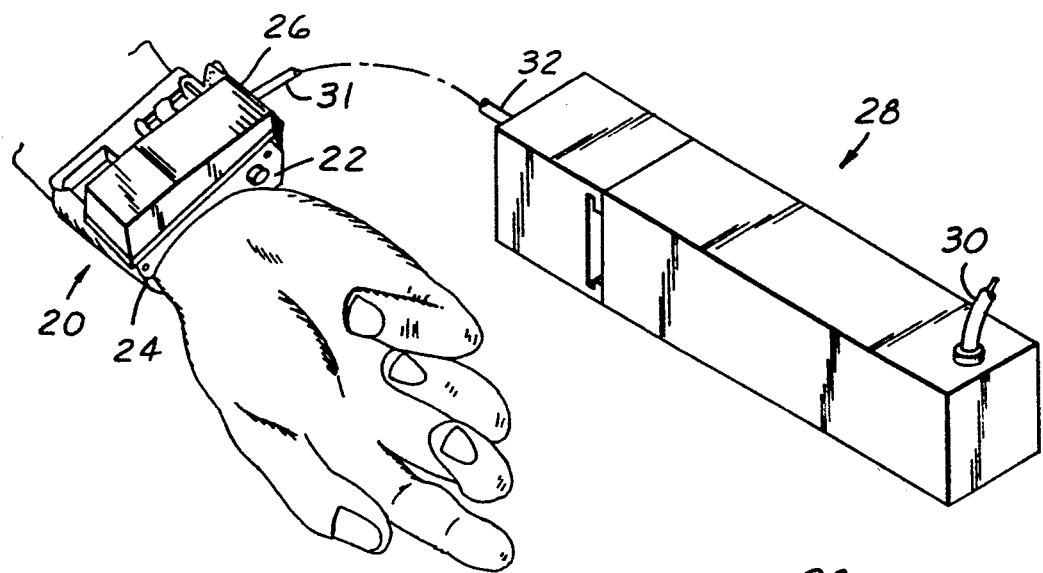
FIG. 1 is a first embodiment of the artery applanation actuator of the present invention.

Now referring to FIG. 1, wrist mount apparatus 20 includes base 22 and flexible strap 24. Flexible strap 24 is adapted to engage base 22 to the wrist of a user. Sensor housing 26 is fastened to base 22 and houses the tissue stress transducer and the means for moving the tissue stress transducer into operative engagement with the tissue overlaying the artery of interest. Fluid displacement source 28 is responsive to electrical signals received via cable 30 to generate a source of displacement fluid and communicate this displacement fluid to sensor housing 26 via tubing 32. It is to be understood, that various electrical signals will be derived from tissue contact stress sensor located within sensor housing 26 and will be made available therefrom via cable 31. These electrical signals carry blood pressure data and will be used to derive intra-arterial blood pressure of the wearer of apparatus 20. Because this invention primarily deals with the device used for applanating the artery of interest, the electrical signals derived from the tissue stress sensor will not be elaborated upon.

Figure 2:
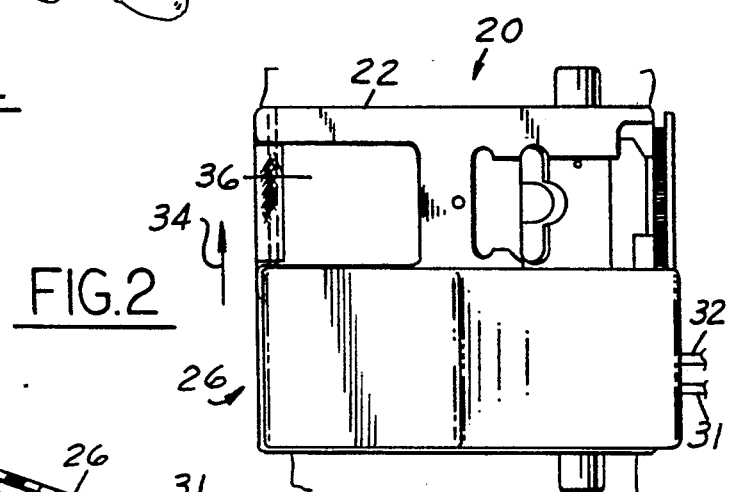
FIG. 2 is a top view of the wrist mount portion of the artery applanation actuator of the present invention.

Now referring to FIG. 2, wrist mount apparatus 20, includes base 22 and sensor housing 26. Apparatus 20 is adapted to be worn on either the right wrist or the left wrist of the wearer, and accordingly sensor housing 26 is adapted to slide between a first use position (first use position shown in FIGS. 1 and 2) for use on the right wrist of a wearer and a second use position for use on the left wrist of a wearer. In the second use position sensor housing 26 slides upwards 34 to completely cover window 36. The details of the applanation apparatus which is housed within sensor housing 26 will now be explained in conjunction with FIGS. 3-5.

Figure 3:
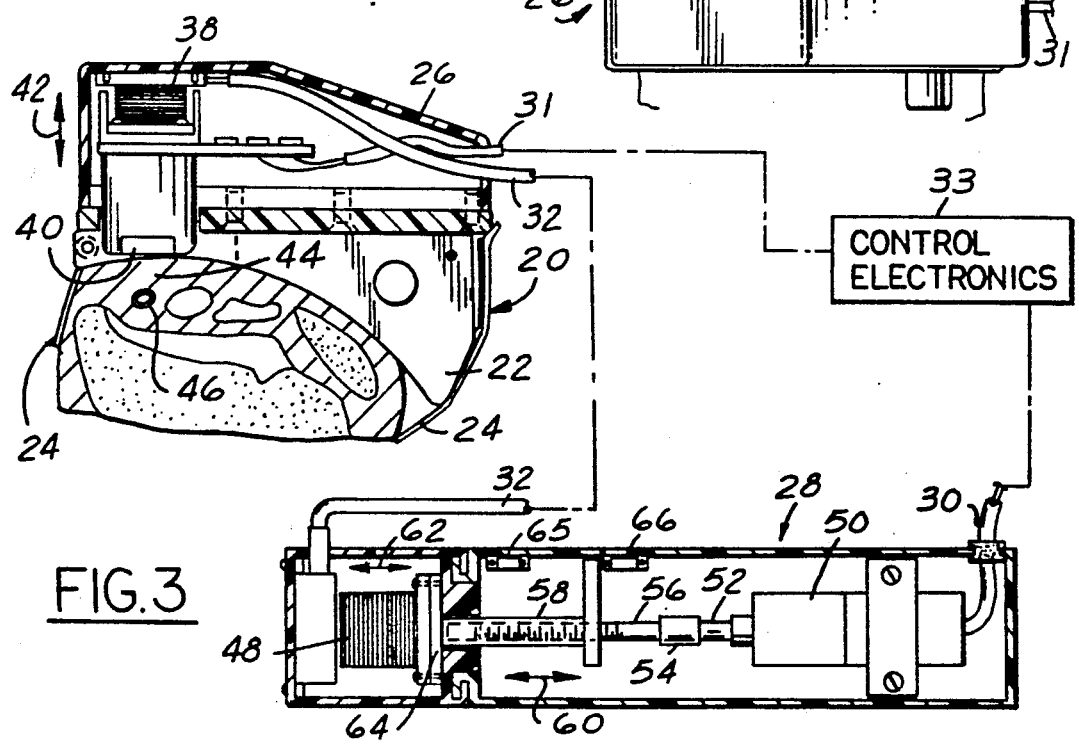
FIG. 3 is a diagrammatic cross-sectional view of the wrist mount portion and the pressurized fluid generating portion of a first embodiment of the artery applanation actuator of the present invention.

Now referring to FIG. 3, sensor housing 26 is mounted to base 22. Within sensor housing 26 is mounted fluid operated slave bellows 38. Bellows 38 is attached to, at one of its ends, tissue contact stress transducer or sensor 40. As bellows 38 receives a displacement fluid from master bellows via tubing 32, it expands downwardly 42, thereby causing tissue stress sensor 40 to engage tissue 44 overlying artery 46. Slave bellows 38 receives displacement fluid from master bellows 48 which is housed within fluid displacement source 28. Electric motor 50 is preferably a rotary motor, but it is recognized that other actuators such as linear electric motors can be used as well. Electric motor 50 is responsive to electrical signals received along cable 30, from said control electronics 33, to rotate its shaft 52. Shaft 52 is coupled to lead screw 56 by way of shaft coupler 54. Lead screw 56 in turn threadedly engages translation nut 58 whereby the rotation of shaft 52 is translated into displacement 60 of translation nut 58. Displacement nut 58, is in turn engages plate 64 o master bellows 48 whereby displacement 60 of translation nut 58 lead directly to collapsing/expanding 62 of master bellows 48. Thus, it can be seen, that when slave bellows 38 is placed in fluid communication with master bellows 48 by way of tubing 32, any displacement 62 of master bellows 48 will result in the corresponding displacement 42 of slave bellows 38. Accordingly, when electrical command signals are received via cable 30, the rotational forces exerted by shaft 52 onto lead screw 56 cause slave bellows 38 to be displaced 42.

Limit switches 65, 66 are placed in operative engagement with the movement of lead screw 58 such that each respective limit switch 65, 66 is activated when lead screw 58 is at either extreme of its permissible travel. Limit switches 65, 66 are well known to those skilled in the art to be general purpose electrical switches which are in turn connected to a controller (controller not shown) which is used to control the electrical signals delivered to motor 50, which, in turn, controls overall applanation process. Preferably, the fluid used within the disclosed artery applanation actuator is hydraulic fluid and tubing 32 is preferably teflon tubing. It is to be understood, however, that other fluid mediums, such as compressed gas, and the like may be used to displace slave bellows 38.

Now referring to FIG. 4, after motor 50 turns upper shaft 52 a predetermined number of revolutions, translation nut 58 will travel along lead screw 56 such that master bellows 48 is at its maximum contraction, thereby placing slave bellows 38 at its maximum extension. When slave bellows 38 is at its maximum extension, tissue 44 overlying artery 46 is depressed thereby flattening artery 46. Thus, it can be seen, that the apparatus of the present invention is particularly suited for applanating an artery of interest.

Fluid pressure source 28 is comprised of two sections, bellows section 68 and motor section 70. Sections 68, 70 are coupled together via connector interface 72. Connector interface 72 can comprise any number of well known quick disconnect type systems. The purpose of quick disconnect 72 is to separate hydraulic circuit comprising tubing 32, slave bellows 38 and master bellows 48 from motor section 70. By providing a means whereby the hydraulic circuit may be separated from motor section 70, the integrity of the hydraulic circuit may be maintained should it ever need to be separated from motor section 70 for the purpose of servicing or storing motor section 70. If no disconnect means 72 was provided to disconnect the motor drive section 70 from the bellows section 68, fluid pressure source 28 would have to be kept with wrist mount apparatus 20 at all times, unless, of course, tubing 32 was disconnected. Disconnecting hydraulic line 32 is generally considered undesirable because of the uncleanliness associated with leaking hydraulic fluid, the possibility of introducing contaminants into the hydraulic circuit and the difficulty associated with bleeding air from the hydraulic circuit when the applanation apparatus is used once more. Thus it can be seen that connector interface 72 is effective for joining bellows section 68 with motor section 70 during normal operating conditions of wrist mount apparatus and is also effective for separating bellows section 68 from motor section 70 for storage or servicing thereby maintaining the integrity of hydraulic circuit 32, 38 and 48.

Now referring to FIG. 4 and FIG. 5, slave bellows 38 is adapted with guide rails 74 and sensor housing 26 is fitted with mating guide slots 76. Guide rails 74 are adapted to engage guide slots 76 thereby allowing slave bellows 38 to freely move upward and downward 42 while still retaining its fixed upright orientation.

Now referring to FIG. 6, in a second embodiment of the present invention, wrist mount apparatus 20 comprises base 22 and sensor housing 26. Unlike the first embodiments shown in FIGS. 1-5 where slave bellows 38 effected the movement of tissue stress sensor 40 within fixed sensor housing 26, sensor housing 26 of FIG. 6 is adapted to pivot about pin 78 thereby placing a tissue stress transducer in operative engagement with the tissue overlying an artery of interest.

Now referring to FIGS. 6 and 7, gear 80 is rigidly fixed to base 22 by way of nonrotating pin 78. Electric motor 82 is comprised of motor housing 84 which is directly attached to mounting plate 93. Mounting plate 93 is fastened within sensor housing 26. Motor output shaft 86 is coupled to gear 80 by way of worm gear 88. Thus it can be seen that when motor shaft 86 rotates, worm gear 88 will engage gear 80 in a way which causes sensor housing (or transducer head portions) 26 to rotate 190 about pin 78. Tissue stress sensor 40 is mounted to sensor housing 26 by way of pivot pin 190. Electrical signals are delivered to and received from sensor 40 by way of electrical cable 92.

Now referring to FIGS. 7, 8 and 9, when electric motor 82 is activated to rotate shaft 86 along a first direction, sensor housing 26 will rotate 190 about pin 78 thereby closing gap 95 and forcing tissue stress sensor 40 in contact with tissue 44 overlying artery 46. As shaft 86 continues to rotate in the first direction past the point of tissue contact depicted in FIG. 8, sensor housing 26 will continue to pivot about pin 78 thereby displacing tissue stress sensor 40 into tissue 44 overlying artery 46 and causing applanation of artery 46. Thus it can be seen that the second embodiment of the artery applanation actuator of the present invention is well suited to applanate an artery of interest.

It can be seen in conjunction with FIGS. 7, 8 and 9 that as housing 26 is rotated about point 78, sensor head 40 pivots about pivot pin 91 thereby keeping engagement face 94 of tissue stress sensor 40 generally tangent to radial artery 46. Thus, it can be seen that the pivotal action of tissue stress sensor 40 about pin 91 acts to prevent outer corner portions 96, 98 of sensor assembly 97 from applying unequal pressure across tissue 44.

Now referring generally to FIGS. 7-9, it is important to note that gear 80 serves a two-fold purpose in the second embodiment of the artery applanation actuator disclosed in FIGS. 7-9. Firstly, gear 80 provides a reaction surface for worm gear 88 thereby enabling housing 26 to pivot 190 about pin 78. Secondly, gear 80 provides, in conjunction with worm gear 88, a gear reduction means whereby the torque required to applanate artery 46 can be accomplished by choosing the correct capacity motor 82 in conjunction with the proper gear reduction ratio of gears 80, 88.

Now referring to FIG. 10, a third embodiment of the artery applanation actuator of the present invention is shown having base 22 connected to a wrist of a user via strap 24. Within base 22 is housed electric motor 82. Electric motor 82 comprises motor housing 84 and motor shaft 86 which extends from motor housing 84 and is secured to sensor housing 26. Thus it can be seen that when motor 84 is made responsive to electrical signals, shaft 86 of motor 82 rotates thereby causing sensor housing 26 to rotate 190. Motor shaft 86 is preferably fitted with gear reduction coupling 100. Gear reduction coupling 100 serves the same purpose as that previously discussed in conjunction with gears 80, 88.

Figure 11:
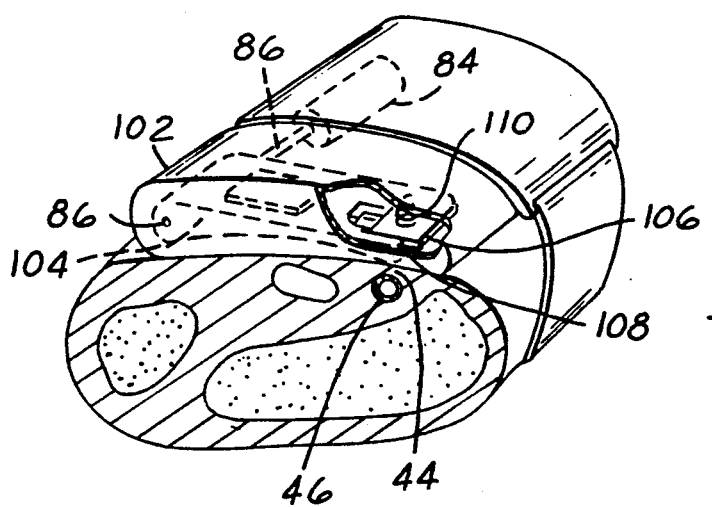
FIG. 11 is a isometric, diagrammatic view of the third embodiment of the artery applanation actuator of the present invention shown on the wrist of a user.
Figure 12:
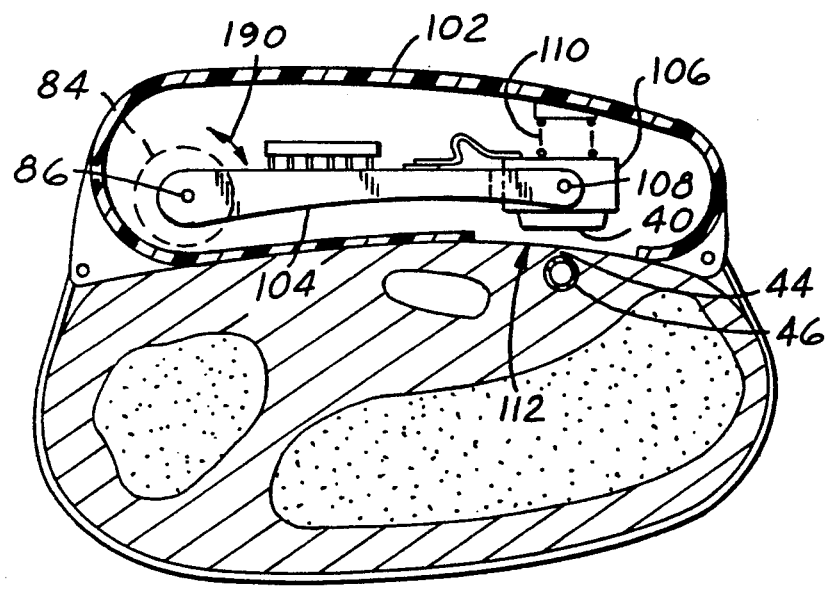
FIG. 12 is a cross-sectional view of the third embodiment of the artery applanation actuator of the present invention shown with the tissue stress sensor head retracted into the outer sheath.

Now referring to FIG. 11, in a preferred embodiment of the artery applanation actuator of FIG. 10, sheath 102 is pivotally mounted to motor shaft 86. Within sheath 102, arm 104 is fixed to shaft 86 and sensor assembly 106 is pivotally connected to arm 104 by way of pivot pin 108. Sensor assembly 106 engages sheath 102 by way of spring 110. Thus, as depicted in FIG. 12, when motor shaft 86 is not applying a downward rotational torque 190 to arm 104, sensor 40 of sensor assembly 106 is retracted into sheath 102 and away from opening 112 thereby protected against inadvertent contact.

Figure 13:
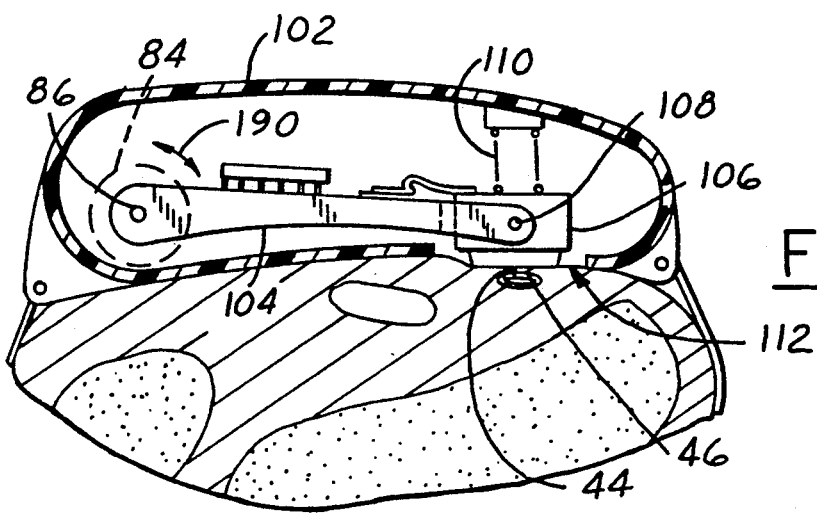
FIG. 13 is a cross-sectional view of the third embodiment of the artery applanation actuator of the present invention shown with the tissue stress transducer extending from the protective sheath.

Now referring to FIG. 13, after motor shaft 86 applies a downward rotational torque 190 of sufficient urging to overcome the force of spring 110, arm 104 will pivot about shaft 86 lowering sensor assembly 106 toward sheath opening 112 thereby placing tissue stress sensor 40 in operative contact with tissue 44 overlying artery 46. Thus, rotational torque 190 exerted by motor shaft 86 on arm 104 is effective for placing sensor 40 in contact with tissue 44 thereby applanating artery 46. Once rotational torque 190 is removed from arm 104, spring 110 urges sensor assembly 106 upwardly thereby retracting sensor 40 away from sheath opening 112 and into the protective recess of sheath 102. Thus it can be seen that the sheathing system of the embodiment disclosed in FIGS. 11-13 is effective for preventing inadvertent contact with sensor 40.

Figure 14:
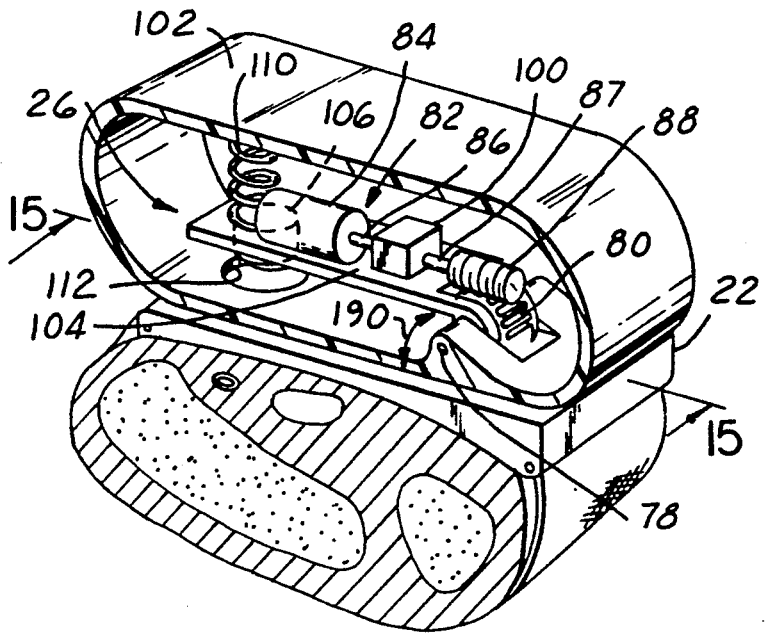
FIG. 14 is a cross-sectional isometric view of a fourth embodiment of the artery applanation actuator of the present invention shown with the tissue stress transducer retracted into the protective sheath.
Figure 15:
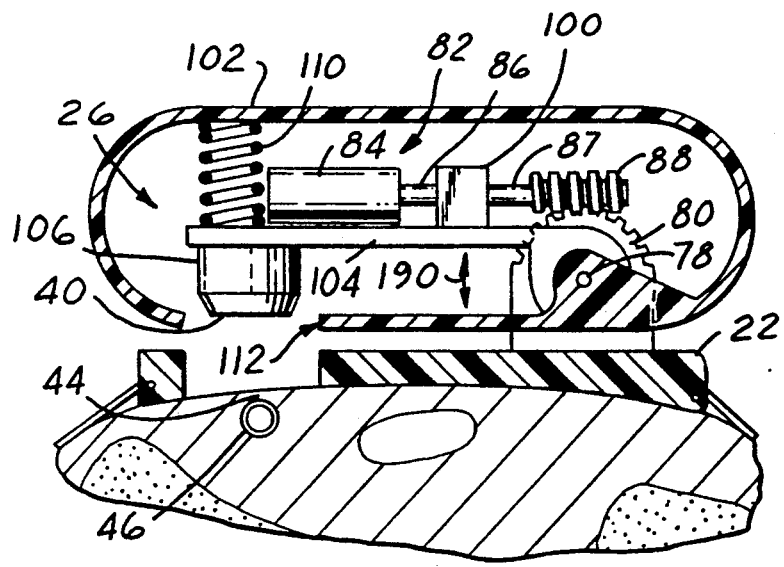
FIG. 15 is a cross-sectional side view of the fourth embodiment of the artery applanation actuator of the present invention shown with the tissue stress transducer retracted into the protective sheath.
Figure 16:
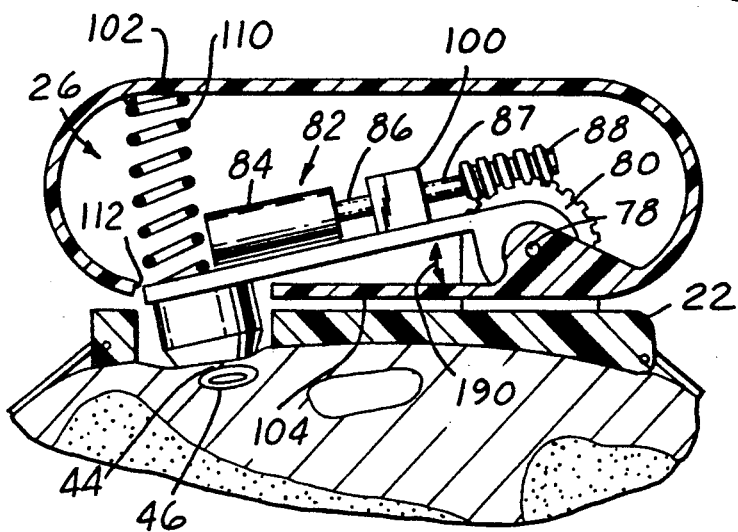
FIG. 16 is a partial cross-sectional view of the fourth embodiment of the artery applanation actuator of the present invention shown with the tissue stress transducer extending through an opening in the protective sheath and contacting the tissue overlying an artery of interest.

Now referring to the fourth embodiment of the artery applanation actuator of the present invention, similar to the embodiment of the present invention set out in FIGS. 6-9, the fourth embodiment of the present invention also houses electric motor 82 on sensor housing 26. The primary difference between the second embodiment set out in FIGS. 6-9 and the fourth embodiment set out in FIGS. 14-16 is the addition of sheath 102 disposed about sensor housing 26 to protect sensor 40 within sensor assembly 106. As depicted in FIGS. 15 and 16, when motor 82 rotates its output shaft 86, gear reduction means 100 is effective for translating the rotation of output shaft 86 into a rotation of shaft 87. Worm gear 88 is fixed to shaft 87 and accordingly translates the rotational motion of shaft 87 to reaction gear 80. Because reaction gear 80 is fixed to base 22 any rotational motion of worm gear 88 translates into rotating 190 sensor housing 26 about pin 78. This rotation of sensor housing 26 causes sensor assembly 106 to pass through sheath opening 112 and engage sensor 40 to tissue 44 overlying artery 46. As this rotational motion is continued the downward force of sensor assembly 106 on tissue 44 causes artery 46 to applanate. Once the rotational torque exerted by motor 82 onto output shaft 86 is extinguished, spring 110 is effective for returning sensor assembly 106 into sheath 102 thereby protecting sensor assembly 106 from inadvertent contact. Thus, it can be seen in conjunction with FIGS. 14-16, that the fourth embodiment of the artery applanation actuator of the present invention is effective for applanating an artery of interest.

The foregoing detailed description shows that the preferred embodiments of the present invention are well suited to fulfill the objects of the invention. It is recognized that those skilled in the art may make various modifications or additions to the preferred embodiments chosen here to illustrate the present invention, without departing from the spirit of the present invention. For example, although the term tissue contact stress sensor (or tissue contact stress transducer) have been used throughout the disclosure of the present invention, it is to be understood that any type of sensor or transducer which is adapted for tonometry use can be employed by the applanation apparatus of the present invention. Accordingly, it is to be understood that the subject matter sought to be afforded protection hereby should be deemed to extend to the subject matter defined in the appended claims, including all fair equivalents thereof.

I claimed:

1. An artery applanation actuator for placing a tissue stress sensor in operative engagement with the tissue overlying an artery of interest, said artery applanation actuator comprising:
   a source of displacement fluid,
   a base portion including means for mounting said base portion to the wrist of a wearer,
   displacing means, coupled to said base portion, and fluidly coupled to said displacement fluid source said displacing means including means for engaging and retaining said tissue stress sensor, said displacing means adapted to respond to a pressure of said fluid in said displacement fluid source and to displace said tissue stress sensor into operative engagement with said tissue overlying said artery of interest, thereby applanating said artery of interest in response to a displacement of said displacement fluid, wherein said displacing means includes a hydraulic bellows.

2. The applanation actuator of claim 1, wherein said source of displacement fluid includes a source of hydraulic fluid and wherein said displacing means further includes a master bellows fluidly coupled to said hydraulic bellows, and a displacement actuator coupled to said master bellows, said master bellows responsive to movement of said displacement actuator to transfer said hydraulic fluid to said hydraulic bellows thereby causing said hydraulic bellows to be responsive to the movement of said displacement actuator.

3. The applanation actuator of claim 2 further including disconnect means disposed between said displacement actuator and said master bellows, whereby said master bellows is separable from said displacement actuator while keeping said master bellows in uninterrupted fluid communication with said slave bellows.

4. The applanation actuator of claim 2, wherein said displacement actuator includes an electric motor and a coupling means, said coupling means coupled between said electric motor and said master bellows for translating mechanical movement of said motor to said master bellows to move said master bellows.

5. The applanation actuator of claim 4, wherein said electric motor includes a rotary electric motor and said coupling includes a threaded shaft connected to said electric motor and a translation nut coupled between said threaded shaft and said master bellows.

6. The applanation actuator of claim 2, wherein said displacing means further includes a flexible tube connected between said master and slave bellows whereby said fluid communication between said master and slave bellows takes place by way of fluid flow within said flexible tube.

7. The applanation actuator of claim 2, wherein said displacement actuator further includes a rotary electric motor and a drive screw, said rotary electric motor including an output shaft coupled to said drive screw and wherein said drive screw is threadedly with said master bellows, and said rotary electric motor is adapted to turn said drive screw thereby displacing said master bellows.

8. The applanation actuator of claim 7, wherein said master and slave bellows include hydraulic bellows filled with hydraulic fluid.

9. An artery applanation actuator for placing a transducer in operative engagement with the tissue overlying an artery of interest, said artery applanation actuator comprising:
   a transducer,
   a base portion including means for mounting said base portion to a body portion of the wearer,
   a transducer head portion for housing said transducer,
   electric motor means having a pivoting output shaft, said electric motor means attached between said base portion and said transducer head portion, for pivoting said transducer head portion thereby causing said transducer to be pivotally moved into operative engagement against said tissue overlying an artery of interest, thereby causing said transducer to applanate said artery of interest.

10. The artery applanation actuator apparatus of claim 9, wherein said electric motor means includes an electric motor having a motor housing rotatably coupled to said pivoting output shaft wherein said electric motor housing is coupled to said transducer head portion and said pivoting output shaft extends from said electric motor housing and engages said base portion.

11. The artery applanation actuator apparatus of claim 10, further including means for pivoting said motor means about said base portion, said pivoting means including a worm gear disposed on said rotary output shaft of said electric motor and a reaction gear fixed to said base portion engaging said worm gear to cause said transducer head portion to pivot about said reaction gear.

12. The artery applanation actuator apparatus of claim 10, further including gear reduction means disposed between said output shaft and said base portion.

13. The artery applanation actuator apparatus of claim 10, further including a protective sheath disposed about said transducer head portion.

14. The artery applanation actuator apparatus of claim 13, wherein said sheath further includes a spring fixed to, and extending from said sheath and attached to said transducer head portion.

15. The artery applanation actuator apparatus of claim 9, wherein said motor means includes an electric motor housing rotatably coupled to said pivoting output shaft wherein said electric motor housing is attached to said base portion and said rotary output shaft extends from said electric motor housing and engages said transducer sensor head portion.

16. The artery applanation actuator apparatus of claim 15, further including gear reduction means coupled between said rotary output shaft of said electric motor and said transducer head portion.

17. The artery applanation actuator apparatus of claim 15, further including a protective sheath disposed about said transducer head portion and pivotally connected about said rotary output shaft.

18. The artery applanation actuator apparatus of claim 17, wherein said sheath further includes a spring fixed to, and extending from said sheath and attached to said transducer head portion.

19. The artery applanation actuator apparatus of claim 18, wherein said transducer head portion includes an arm fixed to said rotary output shaft and a transducer assembly pivotally connected to said arm.

20. The artery applanation actuator apparatus of claim 9, further including a protective sheath disposed about said transducer head portion and pivotally connected to said motor means.

21. A method of applanating an artery using an artery applanation device including a stress sensor mounted to a pivotal arm, wherein said pivotal arm is adapted to pivot about an axis, comprising the steps of:
   (A) mounting said artery applanation device to a body part of a subject,
   (B) pivoting said stress sensor about said axis whereby said sensor is brought into contact with a tissue overlying said artery,
   (C) continuing to pivot said arm after step (B) so as to cause said sensor to applanate said artery, and
   (D) collecting tissue stress data from said stress sensor while said artery is applanated.

* * * * *